(12) United States Patent
Patil

(10) Patent No.: US 12,319,662 B2
(45) Date of Patent: Jun. 3, 2025

(54) COUPLED UREA MELAMINE PLANT

(71) Applicant: Stamicarbon B.V., Sittard (NL)

(72) Inventor: Rahul Patil, Maastricht (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 18/699,960

(22) PCT Filed: Nov. 22, 2023

(86) PCT No.: PCT/NL2023/050610
§ 371 (c)(1),
(2) Date: Apr. 10, 2024

(87) PCT Pub. No.: WO2024/112196
PCT Pub. Date: May 30, 2024

(65) Prior Publication Data
US 2024/0327358 A1  Oct. 3, 2024

(30) Foreign Application Priority Data
Nov. 22, 2022 (EP) ..................................... 22208894

(51) Int. Cl.
| | |
|---|---|
| *C07D 251/60* | (2006.01) |
| *B01D 3/06* | (2006.01) |
| *B01D 53/00* | (2006.01) |
| *B01D 53/14* | (2006.01) |
| *B01D 53/18* | (2006.01) |

(Continued)

(52) U.S. Cl.
CPC ............. *C07D 251/60* (2013.01); *B01D 3/06* (2013.01); *B01D 53/002* (2013.01); *B01D 53/1493* (2013.01); *B01D 53/18* (2013.01); *C07C 273/12* (2013.01); *C07C 273/16* (2013.01); *B01D 2252/2041* (2013.01); *B01D 2252/20431* (2013.01)

(58) Field of Classification Search
CPC ...... C07D 251/60; C07D 251/62; B01D 3/06; B01D 53/002; B01D 53/1493; B01D 53/18; B01D 2252/2041; B01D 2252/20431; C07C 273/12; C07C 273/16; C07C 273/02
USPC ........................................................ 544/201
See application file for complete search history.

(56) References Cited

U.S. PATENT DOCUMENTS

| | | |
|---|---|---|
| 3,161,638 A | 12/1964 | Christoffel et al. |
| 4,565,867 A | 1/1986 | Thomas et al. |
| 6,111,138 A | 8/2000 | Van Wijck et al. |

(Continued)

FOREIGN PATENT DOCUMENTS

| | | |
|---|---|---|
| DE | 102016112944 A1 | 1/2017 |
| EP | 2385043 A1 | 11/2011 |

(Continued)

OTHER PUBLICATIONS

Meessen, Ullmann's Encyclopaedia, chapter Urea, 2010. 39 pages.

(Continued)

*Primary Examiner* — Taylor V Oh
(74) *Attorney, Agent, or Firm* — Leason Ellis LLP

(57) ABSTRACT

The disclosure pertains to a plant and process for the coupled production of urea and melamine. In an embodiment, a lean carbamate solution is supplied from the melamine production section to a recovery section of the urea production section. In an embodiment, enriched carbamate solution from the urea production section is supplied to an off-gas condenser of the melamine production section.

18 Claims, 1 Drawing Sheet

(51) Int. Cl.
*C07C 273/12* (2006.01)
*C07C 273/16* (2006.01)

(56) References Cited

U.S. PATENT DOCUMENTS

| | | |
|---|---|---|
| 6,114,579 A | 9/2000 | Van Wijck |
| 2004/0162429 A1 | 8/2004 | Noe et al. |
| 2015/0119603 A1 | 4/2015 | Van Den et al. |
| 2021/0261498 A1 | 8/2021 | Cavuoti et al. |

FOREIGN PATENT DOCUMENTS

| | | |
|---|---|---|
| EP | 3597641 A1 | 1/2020 |
| WO | 03080584 A1 | 10/2003 |
| WO | 2009109314 A1 | 9/2009 |
| WO | 2020003234 A1 | 1/2020 |
| WO | 2023280684 A1 | 1/2023 |

OTHER PUBLICATIONS

"Urea-melamine plant integration", Nitrogen + Syngas 321, Jan.-Feb. 2013, p. 44-54.
International Search Report for corresponding International Application No. PCT/NL2023/050610, dated Feb. 27, 2024.

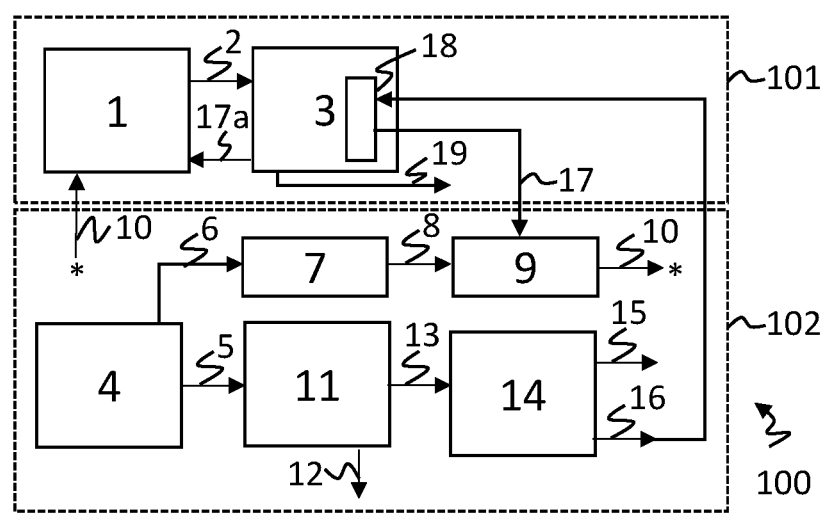

ved NL2023/050610 filed Nov. 22, 2023, which claims
COUPLED UREA MELAMINE PLANT

CROSS-REFERENCE TO RELATED PATENT APPLICATIONS

This application is a U.S. National Stage Application under 35 U.S.C. § 371 of International Patent Application No. PCT/NL2023/050610 filed Nov. 22, 2023, which claims the benefit of priority of European Patent Application numbers 22208894.0 filed Nov. 22, 2022, both of which are incorporated by reference in their entireties.

FIELD

The invention pertains to the coupled, or integrated, production of urea and melamine.

INTRODUCTION

Various types of urea production processes are described in Ullmann's Encyclopaedia, chapter Urea, 2010.

The article "Urea-melamine plant integration", Nitrogen+Syngas 321, January-February 2013, p. 44-54, describes approaches to urea-melamine integration. In illustrated process schemes, aqueous streams from the melamine plant are supplied to a waste water treatment section of the urea plant.

Waste water treatments sections of urea plants are generally based on hydrolysis and desorption and are highly energy consuming.

US 2004/0162429A1 describes a melamine production process of the high pressure non-catalytic type with urea washing of the off-gas. Mother liquor is subjected to a deammoniation treatment giving amongst others an aqueous ammonia solution containing $CO_2$. Water make-up is supplied to the Quenching Column where the melamine stream is quenched.

An example melamine plant is described in EP 2385043A1. The plant uses high pressure non-catalytic melamine synthesis. In FIG. 3 of that document, a washing section for putting streams of anhydrous off-gas in contact with an aqueous washing stream is used. The off-gas, saturated with water, is sent to the urea plant as such or after undergoing a treatment such as condensation by absorption in aqueous solution. The melamine mother liquor is treated in an ammonia recovery section giving an aqueous carbonate (i.e. carbamate) solution which can be sent to a urea plant.

A further example melamine plant is described in EP 3597641. In FIG. 3 of that document, the steam 27 comprising $CO_2$ from the deammoniation treatment is combined with a stream 33 comprising $H_2O$, $NH_3$ and $CO_2$ obtained from a step of decomposition, for instance hydrolysis, of organic components in deammoniated mother liquor; the combined stream can be sent to a urea plant.

It is generally desired to supply off-gas from the melamine plant, containing $CO_2$ and $NH_3$ directly or indirectly to the urea synthesis section where urea is formed by the reaction of $CO_2$ and NH to form carbamate and dehydration of the carbamate. In this way, the production of melamine and urea can be coupled. Typically, the off-gas from the melamine plant is condensed to an aqueous carbamate solution, which is supplied to the synthesis section, in particular if the melamine synthesis pressure is lower than the urea synthesis pressure. However, the presence of water in the synthesis section, in particular in the reaction mixture in the reaction zone, is detrimental to urea yield. The minimum water content of the carbamate solution increases with lower condensation.

SUMMARY

The invention aims to provide for coupling of melamine and urea production with high energy efficiency (relatively low steam consumption) and/or with relatively low supply of water to the urea synthesis section thereby providing for higher urea conversion.

The invention pertains in a first aspect to a process for the coupled production of urea and melamine, comprising: producing urea in a urea synthesis section of a urea production section giving a first urea stream; subjecting said first urea stream to purification in at least a low pressure (LP) recovery section; producing melamine in a melamine synthesis section of the high pressure non-catalytic type, giving molten melamine and anhydrous off-gas, said melamine synthesis section comprised in a melamine production section; washing the anhydrous off-gas by contact with urea in a washing unit and subjecting the washed off-gas to condensation in an off-gas condenser in the melamine production section at a pressure of at least 25 bar to form off-gas condensate, and in a melamine processing section, dissolving the molten melamine in an aqueous solution and crystallizing the melamine with the formation of a stream of crystallized melamine and a stream of mother liquor, and treating a part or all of the mother liquor yielding recovered mother liquor and an aqueous carbamate solution.

The process preferably involves supplying a part or all of said aqueous carbamate solution to a carbamate condenser comprised in said low pressure recovery section, thereby forming enriched carbamate solution. Preferably the process involves supplying at least a part of said enriched carbamate solution directly or indirectly to the off-gas condenser; and supplying said off-gas condensate to said urea synthesis section. Hence, in some embodiments, the process comprises off-gas washing with urea, condensation of anhydrous washed off-gas, and supplying a carbamate solution from an LP carbamate condenser comprised in the LP recovery section to the off-gas condenser, preferably further with supplying the aqueous carbamate solution from the mother liquor treatment to said LP carbamate condenser. The LP carbamate condenser receives a gas stream from the purification step in the LP recovery section.

The invention also pertains to a plant for the coupled production of urea and melamine, comprising a urea production section comprising a urea synthesis section for producing urea giving a first urea stream; a low pressure recovery section for purifying said first urea stream. The plant further comprises a melamine production section comprising: a melamine synthesis section of the high pressure non-catalytic type for producing melamine, giving molten melamine and anhydrous off-gas; a washing unit for washing the anhydrous off-gas by contact with urea; an off-gas condenser for condensing the off-gas at a pressure of at least 25 bar to form off-gas condensate; a melamine processing section comprising a unit for dissolving the molten melamine in an aqueous solution, and a crystallizer for crystallizing the melamine with the formation of a stream of crystallized melamine and a stream of mother liquor; and a treatment unit for treating a part or all of the mother liquor yielding recovered mother liquor and an aqueous carbamate solution. The plant further comprises a liquid flow line for supplying a part or all of said aqueous carbamate solution from said treatment unit to a carbamate condenser comprised in said low pressure recovery section which has an outlet for enriched carbamate solution. The plant preferably comprises a liquid flow line for supplying at least a part of said enriched carbamate solution directly or indirectly to said off-gas condenser, and a liquid flow line for supplying said off-gas condensate to said urea synthesis section. The invention also pertains to a method of modifying an existing plant for the coupled production of urea and melamine.

Accordingly, the invention pertains to a plant and process for the coupled production of urea and melamine, wherein a lean carbamate solution is supplied from the melamine production section to a recovery section of the urea production section and/or enriched carbamate solution from the urea production section is supplied to an off-gas condenser of the melamine production section.

BRIEF DESCRIPTION OF THE DRAWINGS

FIG. 1 schematically illustrates an example process scheme according to the invention.

Any embodiments illustrated in the FIG.(S) are examples only and do not limit the invention.

DETAILED DESCRIPTION

In the inventive process and plant, a carbamate solution is supplied from the melamine production section to the condenser of the LP recovery section, and preferably enriched carbamate solution from the LP recovery section is supplied to an off-gas condenser where the off-gas from the melamine plant is condensed at a higher pressure than the operating pressure of the LP recovery section. The resulting carbamate solution is supplied to the urea synthesis section. Thereby the amount of water supplied to the urea synthesis section is effectively reduced and the load of the waste water treatment section is relatively low, which is advantageous. In the preferred embodiment, the water is used for condensation of carbamate three times: in the melamine production section, in the LP recovery section, and in the off-gas condenser.

The invention pertains to a process and plant for the coupled production of urea and melamine. Herein, coupled indicates that off-gas from the melamine production section is supplied directly or indirectly to the urea synthesis section, in particular after condensation.

In embodiments, the process is also integrated, in that urea melt from the urea production section is supplied to the melamine production section, preferably at least 5%, or at least 10%, or at least 20%, e.g. 10-80 wt. %, 20-70 wt. %, or 30-70 wt. % of the urea formed in the synthesis section is supplied to the melamine production section.

In other embodiments, the melamine production section is fed with urea from an alternative source. Preferably, the amount of urea melt consumed in the melamine production section is at least 10% or at least 20% and/or less than 70% of the amount of urea produced in the urea production section. The remaining part of the urea production is supplied e.g. to a finishing section such as a granulator or prilling tower.

The process comprises producing urea in a urea synthesis section giving a first urea stream; the synthesis is performed at high pressure (above 100 bar absolute) by the reaction of $NH_3$ with $CO_2$. The urea synthesis section, of the plant and process, is e.g. of the type without a high pressure (HP) stripper or of the type with a high pressure stripper, for instance with a $CO_2$ or thermal high pressure stripper. A synthesis section with a HP stripper is preferred; in this embodiment the synthesis section also comprises a HP carbamate condensation section. In a preferred embodiment, the urea synthesis section comprises a HP $CO_2$ stripper.

The synthesis section comprises a reaction zone. The first urea stream comprises urea, water, and ammonium carbamate.

The urea synthesis section comprises a urea synthesis zone, which is provided e.g. by a urea reactor or by a combination vessel comprising a HP condensation section and a reaction section. An example of a combination vessel is a so-called pool reactor. A urea reactor is frequently a vertical reactor with trays, with one or more inlets at the bottom and an outlet for withdrawing a liquid stream comprising urea from a top part of the reactor. The synthesis section preferably has a separate outlet for a gas stream comprising inert gases.

The HP stripper, if used, is a unit for counter-current contact of the urea solution with a gas stream under heating, and is preferably a shell-and-tube heat exchanger with a falling film of urea solution in the tubes and steam in the shell, with a liquid inlet for urea solution to be stripped at the top, a gas outlet at the top connected to the HP carbamate condenser and a liquid outlet at the bottom for urea solution, and in embodiments with a HP $CO_2$ stripper further having an inlet for $CO_2$ feed used as strip gas at the bottom, all connected to the tube side.

In embodiments, the urea synthesis section operates at a pressure at least 10 bar or at least 20 bar higher than the off-gas condenser.

The first urea stream is a urea solution also containing water, carbamate and $NH_3$.

The process involves subjecting the first urea stream to purification in at least a low pressure (LP) recovery section, with optional treatment of the urea solution between the urea synthesis section and the LP recovery section in an MP treatment section. The plant accordingly comprises the LP recovery section.

Purification refers to the removal of components other than urea from the stream. The purification at low pressure preferably involves dissociation of ammonium carbamate in an LP dissociator to give a gas stream comprising $CO_2$ and $NH_3$ which is partially or completely condensed in the LP carbamate condenser. An LP dissociator is typically a heat exchanger, more in particular a shell-and-tube heat exchanger, for example with urea solution to be heated in the stubs and heating fluid, typically steam, in the shell. The LP dissociator has a liquid outlet for purified urea solution and a gas outlet for vapor comprising $NH_3$ and $CO_2$ connected to a LP carbamate condenser, which can also be an absorber, comprised in the LP recovery section.

An MP treatment section, if optionally used in the plant or process, is provided to receive urea solution from the HP synthesis section and with a liquid outlet for urea solution to the LP recovery section. The treatment involves purification of the urea solution by removal of $NH_3$ and $CO_2$, optionally present as carbamate, from the urea solution, at medium pressure. The treatment may involve, for instance, adiabatic flashing, or, for example, heating, or a combination of both in series. The treatment generally involves gas/liquid separation, with the liquid outlet for urea solution connected to the LP recovery section and the gas outlet, for an MP gas stream, connected to an MP carbamate condenser, which can also be an absorber. The MP carbamate condenser is preferably a heat exchanger, configured for indirect heat exchange between urea solution to be heated and the MP gas to be condensed. An MP treatment section with an MP carbamate condenser may be referred to as an MP recovery section. Carbamate solution from the MP carbamate condenser is supplied directly or indirectly to the urea synthesis section.

In an example embodiment, the MP treatment comprises supplying the urea solution at MP through a tube bundle provided in a HP carbamate condenser with condensation of gas from the HP stripper in the shell side space, e.g. as described in US 2015/0119603A1.

The MP carbamate condenser receives typically a part or all of the carbamate solution from the LP carbamate condenser. Preferably, a gas stream comprising inerts from the urea synthesis section is also condensed in the MP carbamate condenser.

The process involves producing melamine in a melamine synthesis section of the high pressure, non-catalytic type, giving molten melamine and anhydrous off-gas; and the plant accordingly comprises the melamine synthesis section. The melamine synthesis is based on the pyrolysis of urea feed into melamine. The melamine synthesis section is comprised in a melamine production section. The melamine synthesis pressure is above 70 bar absolute. The invention is particularly advantageous if the melamine synthesis pressure is at least 10 bar lower than the pressure of the urea synthesis reaction zone, because with such a pressure difference the off-gas is preferably condensed into carbamate solution which can be pumped to the urea synthesis section.

The process involves washing (scrubbing) the anhydrous off-gas from the melamine synthesis by contact with urea (melt) in a (off-gas) washing unit, to recover melamine from the off-gas. The urea melt used for the washing is also used as reactant for the melamine synthesis. The recovered melamine is thereby recycled to the melamine synthesis. The urea used for the washing is supplied as a urea melt. The washed off-gas contains e.g. less than 2 wt. % water or less than 1 wt. % water. The washed off-gas comprises e.g. 45-55 wt. % $NH_3$ and 45-55 wt. % $CO_2$ and less than 2 wt. % water.

The process involves subjecting the washed off-gas to condensation in an off-gas condenser at a pressure of at least 25 bar to form off-gas condensate, preferably an off-gas condensate, preferably at a pressure of at least 50 bar or at least 70 bar or at least 80 bar, or at least 100 bar, and for example at less than 140 bar. The plant accordingly comprises the off-gas condenser. Preferably, the off-gas is condensed at substantially the same pressure as the melamine synthesis pressure (e.g. 0 to 5 bar lower than the melamine synthesis pressure). Condensation of the off-gas at higher pressure is desirable as this permits a lower water content of the formed carbamate solution without risk of precipitation of carbamate. The relatively high condensation pressure enables a condensation temperature of e.g. above 120° C. or even above 140° C., and for example below 160° C.

The off-gas condenser is preferably comprised in the melamine production section. The off-gas condenser is e.g. a heat exchanger raising steam on the cooling fluid side. The steam is for instance used in a steam stripper of the melamine plant, e.g. used for eliminating polycondensates, or e.g. for a hydrolysis unit for purifying an aqueous stream, or for heating mother liquor to be purified. The steam may also be used for steam tracing, e.g. for tracing of the urea melt lines.

The off-gas condenser can for instance also be an absorber, in particular without heat exchange with a cooling fluid, for instance if the melamine production capacity is relatively small compared to the urea production capacity.

The process involves dissolving the molten melamine, typically after one or more purification steps, and crystallizing melamine from the solution with the formation of a stream of crystallized melamine and a stream of mother liquor which is an aqueous liquid stream comprising water, ammonia, and melamine, and typically some urea and oxy-amino-triazines (OAT). The plant accordingly comprises a melamine processing section comprising a unit for dissolving the melamine, e.g. a quench column, and a crystallizer.

The process comprises, for example, contacting the liquid phase from the melamine synthesis unit to contacting with gaseous $NH_3$ to eliminate dissolved $CO_2$ and complete the pyrolysis reaction of urea into melamine in a post-reactor. A background reference for an example of such a step is US 2004/0162429A1. The plant may accordingly comprise a melamine after-reactor.

The process may comprise, for example, dissolving the liquid melamine product, e.g. from said post-reactor, in an aqueous ammonia solution, in a unit for dissolving the molten melamine, for example in a quenching column. A background reference for an example of such a step is US 2004/0162429A1.

The process involves treating a part or all of the mother liquor yielding recovered mother liquor and an aqueous carbamate solution, in a treatment unit. The plant accordingly comprises a treatment unit, in particular a mother liquor treatment unit. Herein, an aqueous carbamate solution refers to an aqueous solution of $NH_3$ and $CO_2$. The treatment of the mother liquor stream to be treated (part or all of the mother liquor) for instance comprises heating of the mother liquor or of an aqueous fraction of the mother liquor, which heating causes the hydrolysis of organic components, such as unreacted urea and melamine, to $CO_2$ and $NH_3$ which are obtained as said aqueous carbamate solution after condensation. The heating step is for instance used for deammoniation of the mother liquor or for decomposition of organic components. In embodiments, two or more heating steps are used with gas/liquid separation which yield gas streams comprising $CO_2$ and $NH_3$ that are recovered as said aqueous carbamate solution, for example a first heating step for deammoniation and a second heating step for decomposition, and the $CO_2$ and $NH_3$ obtained from either or both heating steps is provided as said aqueous carbamate solution after appropriate absorption and/or condensation. For instance, the heating step is carried out in a heating unit with a gas outlet and a liquid outlet, and the gaseous stream from the gas outlet is cooled, e.g. against ambient, preferably with cooling water or with the use of air coolers, with the formation of aqueous carbamate solution.

The process for example involves subjecting a part or all of mother liquor to deammoniation treatment thereby forming a gaseous stream comprising $NH_3$, a carbamate solution, and an aqueous stream comprising deammoniated mother liquor. In some embodiments a part of the mother liquor is recycled directly to the quenching column. The deammoniation treatment is for instance carried out in a deamination column, as described in is US 2004/0162429 A1, and uses for example distillation, as described in U.S. Pat. No. 3,161,638A. The aqueous stream comprising deammoniated mother liquor is for example further processed in a section for the elimination of oxyaminotriazines (OAT), for instance by decomposition into $NH_3$ and $CO_2$, for example as described in EP 2385043A1 and EP 3597641. The gaseous stream comprising $NH_3$ is for instance supplied, suitably after absorption into an aqueous stream, to the quenching column, for reconstituting the mother liquor. The deammoniation treatment hence also serves the purpose of ammonia recovery. At least some of the ammonia comprised in the mother liquor is removed and recovered in the deammoniation treatment. Generally, the treatment may provide for recovery of mother liquor by reconstituting the mother liquor from an ammonia stream and a water stream.

In an embodiment, the treatment hence comprises deammoniating mother liquor thereby forming a gaseous stream comprising $NH_3$, at least a part of said carbamate solution, and an aqueous stream comprising deammoniated mother liquor.

In an embodiment, the treatment hence involves deammoniating said mother liquor thereby forming at least a gaseous stream comprising $NH_3$ and an aqueous stream comprising deammoniated mother liquor, and subjecting at least a part of said deammoniated mother liquor to decomposition, e.g. with hydrolysis, forming a gas stream which is condensed to form at least a part of said carbamate solution. The condensation may involve absorption in an aqueous stream. The gas stream can be contacted with a liquid prior to being condensed.

The process involves supplying a part or all of said aqueous carbamate solution, which is a lean carbamate solution, to a LP carbamate condenser (LPCC) comprised in the LP recovery section and the plant comprises a corresponding liquid flow line for aqueous carbamate solution from the mother liquor treatment unit to the LP carbamate condenser. The gas stream comprising $CO_2$ and $NH_3$ from the LP dissociator is condensed in the LP carbamate condenser, thereby forming enriched carbamate solution. The water fraction of the carbamate solution from the deammoniation treatment is used as solvent for carbamate in the LP carbamate condenser. Preferably at least 50 wt. % of the carbamate solution is supplied to the LPCC. The LP recovery section may comprise two or more LP carbamate condensers in series or in parallel and the carbamate stream, or part thereof, can be supplied to one or more of said LP carbamate condensers. If a part of the carbamate solution is supplied to an LPCC, another part is supplied, for example, to the waste water treatment section of the urea plant, or for instance to a recovery section operated at, e.g. 3 to 20 bar absolute, from where it is recycled to the urea synthesis section.

The carbamate solution supplied from the melamine production section to the LP carbamate condenser of the urea production section has a water content of for instance at least 40 wt. % or at least 45 wt. %, e.g. up to 80 wt. %; and hence is a lean carbamate solution. The carbamate solution as received by the LP carbamate condenser comprises e.g. at least 10 wt. % $NH_3$ and at least 5 wt. % $CO_2$ (amounts including as carbamate). The carbamate solution as received by the LP carbamate condenser comprises e.g. 10-40 wt. % carbamate, e.g. 15-35 wt. %.

The composition of the carbamate solution supplied to the LP carbamate condenser is for instance: 30-60 wt. % water, 20-40 wt. % $NH_3$ and 10-20 wt. % $CO_2$ (amounts including as carbamate).

The LPCC receiving the carbamate solution is preferably operated at a pressure of at least 4.5 bara, more preferably 4.5 to 5.5 bara, to support condensation with a N/C ratio of 3.0 to 3.5 of the formed carbamate solution.

In the event the amount of the carbamate solution supplied the LPCC is smaller, relative to the amount of $CO_2$ and $NH_3$ released in the LP dissociator connected to the LPCC, the N/C ratio of the total formed carbamate solution will be lower. Non-condensed gas from the LPCC can be sent to an atmospheric absorber or atmospheric condenser, as is known in the art.

If appropriate, an MP heating step can be used, as part for the MP treatment section, for instance in a heat exchanger using for example steam as heating fluid, in order to decrease the N/C ratio of the urea solution received by the LP recovery section. Furthermore, the urea solution supplied to the LP dissociator may be contacted with a gaseous stream comprising $CO_2$, e.g., with a gaseous stream having an N/C ratio of less than 2.0, preferably less than 1.6, for example a gas stream as obtained from adiabatic flashing, at medium pressure. Any non-condensed $NH_3$ from the LP recovery section is, for example, absorbed in an (atmospheric) absorber, or is for example subjected to further condensation in an atmospheric condenser, optionally together with other vapours.

Advantageously, the carbamate solution is supplied to the LP carbamate condenser bypassing the (typical) wastewater treatment section of the urea production section, which improves energy efficiency of the plant.

In particular if the carbamate solution from the melamine production section contains carbamate originating from $CO_2$ and $NH_3$ wherein the $CO_2$ is formed and released in a deammoniation column upstream of a decomposition unit of the melamine production section based on hydrolysis, advantageously the corresponding carbamate bypasses both the decomposition unit and the waste water treatment section of the urea production section, thereby increasing energy efficiency.

The enriched carbamate solution from the LP carbamate condenser, or as preferably supplied to the off-gas condenser, for instance has a water content of less than 40 wt. %, such as 20-35 wt. %, and is for example provided a pressure of 4.0 to 8.0 bar, more preferably 4.5 to 5.5 bar.

The amount of make-up water supplied to the LP carbamate condenser, e.g. originating from the WWT, can be reduced by an amount corresponding to the amount of water effectively provided by the lean carbamate solution.

The process preferably involves supplying at least a part, or all, of the enriched carbamate solution directly or indirectly to the off-gas condenser comprised in the melamine production section, where the enriched carbamate solution is contacted with the off-gas to be condensed. The plant accordingly, preferably comprises a corresponding liquid flow line. For instance, a part or all of the enriched carbamate solution is supplied through the optional MP recovery section, in particular through an MP carbamate condenser comprised therein, to the off-gas condenser. Depending on the amount of water required in the off-gas condenser, for instance a part of the carbamate solution from an MP carbamate condenser is supplied to the off-gas condenser. The enriched carbamate solution can be pumped as appropriate. The off-gas condenser may also receive further streams comprising water, e.g. originating from units of the melamine production section. In some embodiments, at least 80% of the water of the carbamate solution at the outlet of the off-gas condenser originates from the enriched carbamate solution. In some embodiments, a first part of the enriched carbamate solution is supplied to the off-gas condenser and a second part of the enriched carbamate solution is supplied to the urea synthesis section bypassing the off-gas condenser.

By virtue of the higher pressure in the off-gas condenser than in the LP carbamate condenser, typically at least 10 bar higher or at least 30 bar higher or at least 60 bar higher, the water fraction of the enriched carbamate solution can act as solvent for the carbamate formed by the condensation of the off-gas from the melamine synthesis, even if the enriched carbamate solution has a water content (wt. %) not substantially higher than the minimum water content permitted in the LP carbamate condenser.

In an alternative embodiment, only one or more aqueous streams other than said enriched carbamate solution are supplied to the off-gas condenser, to provide absorbent for the off-gas to be condensed. In further embodiments, at least a part, or all, of the enriched carbamate solution directly or indirectly to the off-gas condenser comprised in the melamine production section, and other aqueous streams are supplied to the carbamate condenser.

The process preferably involves supplying the off-gas condensate, i.e. carbamate solution, from the off-gas condenser to said urea synthesis section. The off-gas condensate is for instance supplied directly or indirectly to the urea reaction zone, for instance to the urea reactor or to a high pressure carbamate condenser comprised in the synthesis section. The supplied carbamate is accordingly converted in to urea in the urea synthesis section. The water fraction of the off-gas condensate (carbamate solution) is detrimental to urea yield and is advantageously relatively low. The off-gas condensate is preferably supplied, e.g. pumped, to the urea synthesis section operating at a pressure preferably at least 10 bar or at least 20 bar higher than the off-gas condenser. For the preferred embodiments wherein the off-gas condenser operates at pressures of above 40 bar or above 50 bar, the off-gas condensate comprises for instance 5 to 20 wt. % water, e.g. 10 to 15 wt. % water. The skilled person can determine the required pressure to achieve these water levels. The off-gas condensate comprises e.g. 40-50 wt. % $NH_3$ and 40-50 wt. % $CO_2$.

Urea solution from the LP recovery section is supplied least in part to an evaporation section, comprising one or more evaporators, where water is evaporated to form a urea melt. In some embodiments, a part of the urea melt is supplied to the melamine plant and a part is supplied to a finishing section. Preferably a part of all of the urea melt is supplied to the melamine production section. The vapor stream from the evaporation section is condensed in a condensation section. The process condensate from the condensation section is supplied to a wastewater treatment section (also known as process condensate treatment section) for purification where the urea, $NH_3$ and $CO_2$ (also as carbamate) contained in it are removed by hydrolysis and desorption, to provide clean process condensate. This purification step is, generally, highly energy consuming.

An example plant and process, which do not limit the invention, is schematically illustrated in FIG. 1. The plant (100) comprises a urea production section (101) and a melamine production section (102). The urea production section (101) comprises a urea synthesis section (1) and LP recovery section (3).

The melamine production section comprises a melamine synthesis section (4), a washing unit (7), an off-gas condenser (9), a melamine processing section (11), and a treatment unit (14) (mother liquor treatment section).

Urea is produced in the urea synthesis section (101) by reacting $CO_2$ and $NH_3$ giving a first urea stream (2), in particular urea solution, also comprising water and carbamate. The first urea stream is purified in at least a LP recovery section (3), preferably in an MP and LP recovery section in series, to decompose and remove at least carbamate from the urea stream to give a purified urea solution (19). In the melamine production section (102), melamine is produced by pyrolysis of urea in a melamine synthesis section (4) of the high pressure non-catalytic type, giving molten melamine (5) and anhydrous off-gas (6). The anhydrous off-gas is washed (or scrubbed) by contact with urea (in particular, urea melt) in a washing unit (7). The washed off-gas (8) is condensed in an off-gas condenser (9) at a pressure of at least 25 bar, preferably at least 60 bar or at least 70 bar, to form off-gas condensate (10) which typically is a high pressure (<70 bar) carbamate solution. The molten melamine (5) is dissolved in a melamine processing section (11) in an aqueous solution and the melamine is crystallized rom the solution with the formation of a stream of crystallized melamine (12) and a stream of mother liquor (13). A part or all of the mother liquor is treated (14) to obtain recovered mother liquor (15) and an aqueous carbamate solution (16). A part or all of the carbamate solution (16) is supplied, e.g. pumped, to the LP carbamate condenser (18) comprised in the LP recovery section (3), thereby forming enriched carbamate solution (17), by way of the condensation of the gas stream from the LP dissociator of the LP recovery section. A first part of the enriched carbamate solution (17) is supplied directly to the off-gas condenser (9), and the off-gas condensate (10) (carbamate solution) from the off-gas condenser is supplied to said urea synthesis section. A second part of the enriched carbamate solution (17a) is supplied to the urea synthesis section (1), preferably through an MP recovery section (not shown).

The invention also provides method of modifying an existing plant for the coupled production of urea and melamine. With a reference to FIG. 1 which does not limit the invention, the existing plant comprises, as discussed in connection with the inventive process and plant, a urea production section (101) comprising a urea synthesis section (1) and a low pressure recovery section (3) for purifying the first urea stream, the section comprising a LP carbamate condenser (18) with an outlet for enriched carbamate solution (17). The existing plant also comprises, as discussed in connection with the inventive plant, a melamine production section (102) comprising a melamine synthesis section (4), the off-gas washing unit (7), the off-gas condenser (9) for condensing the off-gas (8) configured to operate at a pressure of at least 25 bar to form off-gas condensate (10), and the melamine processing section (11) which comprises a unit for dissolving the molten melamine in an aqueous solution, and the crystallizer for crystallizing the melamine with the formation of a stream of crystallized melamine (12) and a stream of mother liquor (13). The melamine production section (102) further comprises a treatment unit (14) for treating a part or all of the mother liquor (13) yielding recovered mother liquor (15) and an aqueous carbamate solution (16). The existing plant comprises a liquid flow line from an outlet of off-gas condenser (9) for said off-gas condensate (10) to an inlet of said urea synthesis section. The method of modifying the existing plant comprises providing the plant with a liquid flow line from an outlet of said a treatment unit (14) for said carbamate solution (16) to said carbamate condenser (18) comprised in said low pressure recovery section (3); and preferably providing the plant with a liquid flow line from an outlet for said enriched carbamate solution (17) of the LP carbamate condenser (18) directly or indirectly to the off-gas condenser (9). In other methods of modifying an existing urea plant, the melamine production section is added, and coupled using the liquid flow lines as specified. The inventive plant is, however, also very suitable as a grassroot plant.

The term 'carbamate', as used herein, refers to ammonium carbamate, as that term is used in the field of urea production. In aqueous carbamate streams, the component can be present as carbonate species. Amounts of $NH_3$ and $CO_2$ for aqueous streams include the amounts present as carbonate species.

As used herein, for process streams of the urea production section (i.e. not for steam lines; neither for melamine production section), high pressure (HP) is above 100 bar, for instance 120 to 300 bar, for example 140 to 200 bar. Medium pressure (MP) is for example 10 to 80 bar (including intermediate pressure of 30 to 70 bar), in particular 15 to 30 bar, and low pressure (LP) is for example 0 to 10 bar, in particular 1 to 8 bar or 2 to 5 bar. All pressures are bar absolute (bara).

The term 'typical' and 'in particular' are used to indicate features that can be used in some embodiments but that are not mandatory. Also preferred features are not mandatory.

The N/C ratio for gas streams indicates the molar ratio of $NH_3$ to $CO_2$. The N/C ratio as used herein for the urea synthesis section reflects the composition of the so-called initial mixture before urea production, consisting only of NHB, $CO_2$ and $H_2O$, as used in the art of urea plants, and is the molar ratio $NH_3$ to $CO_2$. The N/C ratio carbamate solution indicates the molar ratio of the corresponding amounts of $NH_3$ to $CO_2$. The N/C ratio for carbamate condenser refers to the N/C ratio of the carbamate solution at the liquid outlet. The H/C ratio section reflects the composition of the so-called initial mixture before urea production, consisting only of $NH_3$, $CO_2$ and $H_2O$, as used in the art of urea plants, and is the molar ratio $H_2O$ to $CO_2$.

The term 'melamine off-gas' as used herein indicates off-gas from the melamine production section and refers to a gas stream mainly containing $NH_3$, $CO_2$, and possibly $H_2O$.

The term 'first' as used herein for a unit or step permits the presence of further, upstream, instances of such unit or step.

A liquid flow line, as used herein, indicates a flow line for transport of liquid streams, the fluid being in the liquid state through the entire liquid flow line, and does not include flow lines for transport of gaseous stream.

All preferences and details discussed in connection with the process, apply also for the plant, and vice versa. All preferences and details described in connection with the plant, apply also for the method of modifying a plant.

Embodiments of the invention will now be further illustrated by the following example(s) which do not limit the invention or the claims.

Example 1

A 3790 MTPD urea plant of the HP $CO_2$ stripping type is coupled to a melamine production section with, for example, 30 wt. % of urea supplied to a non-catalytic high pressure melamine production section with melamine synthesis pressure of 110 bar and urea washing of the off gas. The coupled plant is schematically illustrated in FIG. 1.

Carbamate solution (A) (at about 50° C.) from a deammoniation unit for mother liquor of the melamine production section was supplied to the LP carbamate condenser operated at about 65° C. The resulting enriched carbamate solution (B) is supplied for a part B1 to the melamine off-gas condenser operated at 110 bar and about 150° C. also receiving essentially anhydrous off-gas form melamine synthesis (C); the remaining part B2 of the enriched carbamate solution is supplied to an MP recovery section operated at 25 bar. The carbamate solution (D) formed in the off-gas condenser is supplied to the urea synthesis section. The compositions of the streams were as given in Table 1.

Advantageously, 5.5 ton/hr water is supplied in the example from the melamine plant to the LP carbamate condenser without need for energy-consuming treatment in a waste water treatment section in a urea production section.

It can be seen that in the example, 7.6 ton/hr water is supplied as part of the enriched carbamate solution to the off-gas condenser and thereby used effectively twice, compared to a reference embodiment wherein the enriched carbamate solution is supplied entirely to the urea synthesis section, optionally through an MP recovery section operating at 25 bar. The LP carbamate condenser received make-up water as appropriate.

Compared to a reference plant wherein all enriched carbamate solution is supplied to the MP recovery section and lean carbamate solution is supplied directly to the off-gas condenser, the water recycle to the urea synthesis section is reduced by 3.4 ton/hr (from 50.0 ton/hr to 46.5 ton/hr, 7% relative reduction).

The H/C ratio in the urea synthesis section was 0.62 in the inventive plant compared to 0.67 in a comparative plant where carbamate solution from the recovery section is supplied directly to the synthesis section. This increases the conversion in the rector by additional 0.5 wt. % urea and reduces the steam need at the high pressure stripper by 20 to 25 kg steam/ton of urea for equivalent stripping efficiency.

TABLE 1

| Stream | | | Pressure | Flow rate | $H_2O$ | $NH_3$ | $CO_2$ |
|---|---|---|---|---|---|---|---|
| (**) | | Description | (bara) | (ton/hr) | wt. % (*) | | |
| A | 16 | lean carb. sol. | | 10.8 | 50 | 37 | 13 |
| B | 17 + 17a | enriched carb. sol. | 5 | 141 (*) | 30 | 37 | 33 |
| B1 | 17 | B to off-gas condenser | 5 | 25 | 30 | 37 | 33 |
| C | 8 | off-gas (gaseous) | >80 | 33.4 | <0.2 | 48 | 51 |
| D | 10 | HP carb. sol. | >80 | 58 | 13.7 | 43 | 43 |

(*) $NH_3$ and $CO_2$ also as carbamate in liquid streams;
(**) reference in FIG. 1.

The invention claimed is:

1. A process for the coupled production of urea and melamine, comprising:
   producing urea in a urea synthesis section of a urea production section giving a first urea stream;
   subjecting said first urea stream to purification in at least a low pressure recovery section;
   producing melamine in a high pressure non-catalytic melamine synthesis section, giving molten melamine and anhydrous off-gas, said melamine synthesis section comprised in a melamine production section;
   washing the anhydrous off-gas by contact with urea in a washing unit and subjecting the washed off-gas to condensation in an off-gas condenser in the melamine production section at a pressure of at least 25 bar to form off-gas condensate;
   in a melamine processing section, dissolving the molten melamine in an aqueous solution and crystallizing the melamine with the formation of a stream of crystallized melamine and a stream of mother liquor, and treating a part or all of the mother liquor yielding recovered mother liquor and an aqueous carbamate solution;
   supplying a part or all of said aqueous carbamate solution to a carbamate condenser comprised in said low pressure recovery section, thereby forming enriched carbamate solution
   supplying at least a part of said enriched carbamate solution directly or indirectly to the off-gas condenser.

2. The process according to claim 1, further comprising: supplying said off-gas condensate to said urea synthesis section.

3. The process according to claim 1, wherein the treatment of mother liquor comprises:

deammoniating mother liquor thereby forming a gaseous stream comprising $NH_3$, at least a part of said carbamate solution, and an aqueous stream comprising deammoniated mother liquor.

4. The process according to claim 1, wherein the treatment of mother liquor comprises:
deammoniating said mother liquor thereby forming at least a gaseous stream comprising $NH_3$ and an aqueous stream comprising deammoniated mother liquor, and subjecting at least a part of said deammoniated mother liquor to decomposition forming a gas stream which is condensed to form at least a part of said carbamate solution.

5. The process according to claim 1, wherein the urea synthesis section comprises a high pressure $CO_2$ stripper.

6. The process according to claim 5, wherein the purification of the first urea stream involves adiabatic flashing of the urea stream at medium pressure (MP), optionally with further heating at medium pressure, the flashing and optional heating giving a first urea solution that is supplied to the low pressure recovery section, and a MP gas stream supplied to an MP carbamate condenser.

7. The process according to claim 6, wherein said enriched carbamate solution is supplied in a part or entirely to said MP carbamate condenser.

8. The process according to claim 1, wherein the off-gas condenser is operated at a pressure of at least 80 bar.

9. The process according to claim 1, the urea synthesis section operates at a pressure at least 10 bar or at least 20 bar higher than the off-gas condenser.

10. The process according to claim 1, wherein at least 10 wt. % of the urea formed in the synthesis section supplied to the melamine production section.

11. A plant for the coupled production of urea and melamine, comprising:
a urea production section comprising
a urea synthesis section for producing urea giving a first urea stream;
a low pressure recovery section for purifying said first urea stream; and
a melamine production section comprising:
a high pressure non-catalytic melamine synthesis section for producing melamine, giving molten melamine and anhydrous off-gas;
a washing unit for washing the anhydrous off-gas by contact with urea;
an off-gas condenser for condensing the off-gas at a pressure of at least 25 bar to form off-gas condensate;
a melamine processing section comprising a unit for dissolving the molten melamine in an aqueous solution, and a crystallizer for crystallizing the melamine with the formation of a stream of crystallized melamine and a stream of mother liquor; and
a treatment unit for treating a part or all of the mother liquor yielding recovered mother liquor and an aqueous carbamate solution,
wherein the plant comprises a liquid flow line for supplying a part or all of said aqueous carbamate solution to a carbamate condenser comprised in said low pressure recovery section which has an outlet for enriched carbamate solution, and a liquid flow line for supplying at least a part of said enriched carbamate solution directly or indirectly to said off-gas condenser.

12. The plant according to claim 11, comprising a liquid flow line for supplying said off-gas condensate to said urea synthesis section.

13. The plant according to claim 11, wherein the treatment unit comprises a column for deammoniating said mother liquor, having a gas outlet for a gaseous stream comprising $NH_3$ and a liquid outlet for an aqueous stream comprising deammoniated mother liquor, and a decomposition unit for subjecting at least a part of said deammoniated mother liquor to decomposition, having a gas outlet for a gas stream which is connected to a condensation unit for condensing said gas stream to form at least a part of said carbamate solution.

14. The plant according to claim 11, wherein the urea synthesis section comprises a high pressure $CO_2$ stripper.

15. A method of modifying an existing plant for the coupled production of urea and melamine, the existing plant comprising:
a urea production section comprising
a urea synthesis section for producing urea giving a first urea stream;
a low pressure recovery section for purifying said first urea stream, comprising a carbamate condenser with an outlet for enriched carbamate solution;
a melamine production section comprising:
a high pressure non-catalytic melamine synthesis section of the high pressure non catalytic type for producing melamine, giving molten melamine and anhydrous off-gas;
a washing unit for washing the anhydrous off-gas by contact with urea
an off-gas condenser for condensing the off-gas at a pressure of at least 25 bar to form off-gas condensate;
a melamine processing section comprising a unit for dissolving the molten melamine in an aqueous solution, and a crystallizer for crystallizing the melamine with the formation of a stream of crystallized melamine and a stream of mother liquor, and
a treatment unit for treating a part or all of the mother liquor yielding recovered mother liquor and an aqueous carbamate solution,
and a liquid flow line from an outlet of off-gas condenser for said off-gas condensate to an inlet of said urea synthesis section;
the method comprising: providing the plant with a flow line from an outlet of said treatment unit for said aqueous carbamate solution to said carbamate condenser comprised in said low pressure recovery section; and preferably providing a liquid flow line from an outlet for said enriched carbamate solution directly or indirectly to said off-gas condenser.

16. A process for the coupled production of urea and melamine, comprising: producing urea in a urea synthesis section of a urea production section giving a first urea stream; subjecting said first urea stream to purification in at least a low pressure (LP) recovery section; producing melamine in a high pressure non-catalytic melamine synthesis section, giving molten melamine and anhydrous off-gas, said melamine synthesis section comprised in a melamine production section; washing the anhydrous off-gas by contact with urea in a washing unit and subjecting the washed off-gas to condensation in an off-gas condenser in the melamine production section at a pressure of at least 25 bar to form off-gas condensate, and in a melamine processing section, dissolving the molten melamine in an aqueous solution and crystallizing the melamine with the formation of a stream of crystallized melamine and a stream of mother liquor, and treating a part or all of the mother liquor yielding recovered mother liquor and an aqueous carbamate solution; wherein the process further comprises: supplying a carbamate solution from an LP carbamate condenser comprised in the LP recovery section to the off-gas condenser, wherein the LP carbamate condenser receives a gas stream from the purification step in the LP recovery section.

17. The process according to claim 16, further comprising: supplying the aqueous carbamate solution from the mother liquor treatment to said LP carbamate condenser.

18. The process according to claim 7, wherein said enriched carbamate solution is supplied in a part or entirely to said MP carbamate condenser and from said MP carbamate condenser to said off-gas condenser.

\* \* \* \* \*

UNITED STATES PATENT AND TRADEMARK OFFICE
CERTIFICATE OF CORRECTION

| | |
|---|---|
| PATENT NO. | : 12,319,662 B2 |
| APPLICATION NO. | : 18/699960 |
| DATED | : June 3, 2025 |
| INVENTOR(S) | : Rahul Patil |

It is certified that error appears in the above-identified patent and that said Letters Patent is hereby corrected as shown below:

In the Claims

At Column 14, Lines 23-26, "a high pressure non-catalytic melamine synthesis section of the high pressure non catalytic type for producing melamine, giving molten melamine and anhydrous off-gas;" should be changed to -- a high pressure non-catalytic melamine synthesis section for producing melamine, giving molten melamine and anhydrous off-gas; --

Signed and Sealed this
Twenty-ninth Day of July, 2025

Coke Morgan Stewart
*Acting Director of the United States Patent and Trademark Office*